(12) United States Patent
Jeon et al.

(10) Patent No.: US 10,473,567 B2
(45) Date of Patent: Nov. 12, 2019

(54) CELL COLLECTING DEVICE

(71) Applicant: CYTOGEN CO., LTD., Seongnam-si, Gyeonggi-do (KR)

(72) Inventors: Byung Hee Jeon, Seongnam-si (KR); Jong Kil Lee, Incheon (KR)

(73) Assignee: CYTOGEN CO., LTD., Seongnam-si (KR)

(*) Notice: Subject to any disclaimer, the term of this patent is extended or adjusted under 35 U.S.C. 154(b) by 149 days.

(21) Appl. No.: 15/349,922

(22) Filed: Nov. 11, 2016

(65) Prior Publication Data
US 2017/0059460 A1  Mar. 2, 2017

Related U.S. Application Data

(63) Continuation of application No. 13/881,719, filed as application No. PCT/KR2011/007976 on Oct. 25, 2011, now abandoned.

(30) Foreign Application Priority Data

Oct. 25, 2010 (KR) .................. 10-2010-0104249
Oct. 25, 2010 (KR) .................. 10-2010-0104250

(51) Int. Cl.
*G01N 1/40* (2006.01)
*A61M 1/34* (2006.01)
(Continued)

(52) U.S. Cl.
CPC .............. *G01N 1/4005* (2013.01); *A61M 1/34* (2013.01); *A61M 1/341* (2014.02); *B01D 39/10* (2013.01);
(Continued)

(58) Field of Classification Search
None
See application file for complete search history.

(56) References Cited

U.S. PATENT DOCUMENTS 1,801,934 A * 4/1931 Pearson ............... B65F 1/02
210/464
3,834,539 A 9/1974 Thompson
(Continued)

FOREIGN PATENT DOCUMENTS

CN 101329231 A 12/2008
CN 101785883 A 7/2010
(Continued)

OTHER PUBLICATIONS

International Search Report dated May 21, 2012 of PCT/KR2011/007976 which is the parent application—2 pages.
(Continued)

*Primary Examiner* — Benjamin M Kurtz
(74) *Attorney, Agent, or Firm* — Novick, Kim & Lee, PLLC; Jae Youn Kim (57) ABSTRACT

A cell collecting device is configured to collect target cells from a fluid sample such as blood or physiological fluid. The cell collecting device includes a conduit through which a fluid sample containing target cells passes. The cell collecting device further includes a screen filter installed inside the conduit and configured to guide the target cells toward a specified region. The screen filter includes a plurality of filtering holes for filtering the target cells.

10 Claims, 10 Drawing Sheets

(51) Int. Cl.
*B01D 39/10* (2006.01)
*C12M 1/00* (2006.01)

(52) U.S. Cl.
CPC ..... *C12M 47/04* (2013.01); *A61M 2205/3334* (2013.01); *G01N 2001/4016* (2013.01)

(56) References Cited

U.S. PATENT DOCUMENTS

| | | | |
|---|---|---|---|
| 4,264,446 | A | 4/1981 | Fregeau |
| 5,043,082 | A * | 8/1991 | Hermann, Jr. ......... B01D 61/18 |
| | | | 210/451 |
| 5,240,861 | A | 8/1993 | Bieri |
| 5,861,094 | A * | 1/1999 | Goehde .................. C12M 33/14 |
| | | | 210/232 |
| 5,944,991 | A | 8/1999 | Shellenbarger et al. |
| 2007/0025883 | A1 | 2/2007 | Tai et al. |
| 2009/0188864 | A1 | 7/2009 | Zheng et al. |
| 2009/0314724 | A1 | 12/2009 | Nierich |

FOREIGN PATENT DOCUMENTS

| | | |
|---|---|---|
| JP | 2006-305517 A | 11/2006 |
| JP | 2012-65590 A | 4/2012 |
| KR | 20-1993-0023900 U | 11/1993 |

OTHER PUBLICATIONS

Chinese Office Action dated Mar. 26, 2014 of corresponding Chinese Patent Application No. 201180062660.7—14 pages.
Chinese Office Action dated Jan. 29, 2015 of corresponding Chinese Patent Application No. 201180062660.7—14 pages.
Office Action dated Jun. 20, 2012 of corresponding Korean Patent Application No. 10-2010-0104250—3 pages.
Office Action dated May 8, 2012 of corresponding Korean Patent Application No. 10-2010-0104249—3 pages.
Office Action dated Sep. 24, 2015 of corresponding Japanes Patent Application No. 2013-536504—3 pages.

* cited by examiner

CELL COLLECTING DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The present invention relates to a cell collecting device and, more particularly, to a cell collecting device capable of filtering and collecting target cells from a fluid sample such as blood or physiological fluid.

BACKGROUND OF THE INVENTION

In recent years, regulations are increasingly strengthened on a biological test and a clinical test conducted for the sake of treatment of human diseases. As an alternative for the biological test and the clinical test, research and development have been extensively made on the collection of live cells from the human blood. The collection of cells is conducted by different kinds of cell collecting devices such as a micro-fluidic device, a CTC (Circulating Tumor Cell) chip, a filter, and so forth.

A filter for filtering cells from blood is disclosed in many patent documents, e.g., U.S. Patent Publication Nos. 2007/0025883A1 and 2009/0188864A1. The filter is formed of a membrane having a plurality of pores for filtering cells. In the technologies of the aforementioned patent documents, cancer cells are dispersed over the entire surface of the filer mounted inside a chamber or a central square hole. For that reason, there is a problem in that it becomes difficult to identify the filtered state of the cancer cells. Moreover, it is difficult to recover and collect the cancer cells dispersed on the surface of the filter.

SUMMARY OF THE INVENTION

Technical Problems

In view of the problems noted above, it is an object of the present invention to provide a cell collecting device capable of filtering target cells from a fluid sample such as blood or physiological fluid and collecting the target cells in a region near a tubular wall.

Another object of the present invention is to provide a cell collecting device capable of gathering target cells at a specified place and collecting the target cells with ease.

Means for Solving the Problems

In order to achieve these objects, the present invention provides a cell collecting device, including: a conduit through which a fluid sample containing target cells passes; and a screen filter installed inside the conduit and configured to guide the target cells toward a specified region, the screen filter including a plurality of filtering holes for filtering the target cells.

The conduit may include a tubular wall defining a passage for passing the fluid sample therethrough, the screen filter configured to guide the target cells toward a boundary region where the screen filter meets with the tubular wall. The screen filter may be obliquely installed in the passage along a flow direction of the fluid sample. The screen filter may include a trap formed at a downstream end of the screen filter so as to gather the target cells. The screen filter may be formed into a curvilinear shape. The conduit may include an outlet formed near the boundary region and kept in communication with the boundary region so that the target cells can be discharged through the outlet. The screen filter may include a convex portion formed to guide the target cells toward the boundary region. The screen filter may include a concave portion formed to guide and gather the target cells. The concave portion may be formed at a center of the screen filter so as to gather the target cells. The screen filter may further include a trap formed at a center of the concave portion so as to receive the target cells.

Advantageous Effects of the Invention

The present cell collecting device is capable of separating target cells from a fluid sample, gathering the target cells at a specified place and collecting the target cells with ease. This significantly increases the collecting percentage of the target cells. Accordingly, the present cell collecting device is useful in collecting target cells from the human blood for the purpose of analysis, inspection, drug trials and clinical tests.

DETAILED DESCRIPTION OF THE PREFERRED EMBODIMENTS

Other objects, specific advantages and novel features of the present invention will become apparent from the following description of preferred embodiments made in conjunction with the accompanying drawings.

Certain preferred embodiments of a cell collecting device according to the present invention will now be described in detail with reference to the accompanying drawings.

Figure 1:
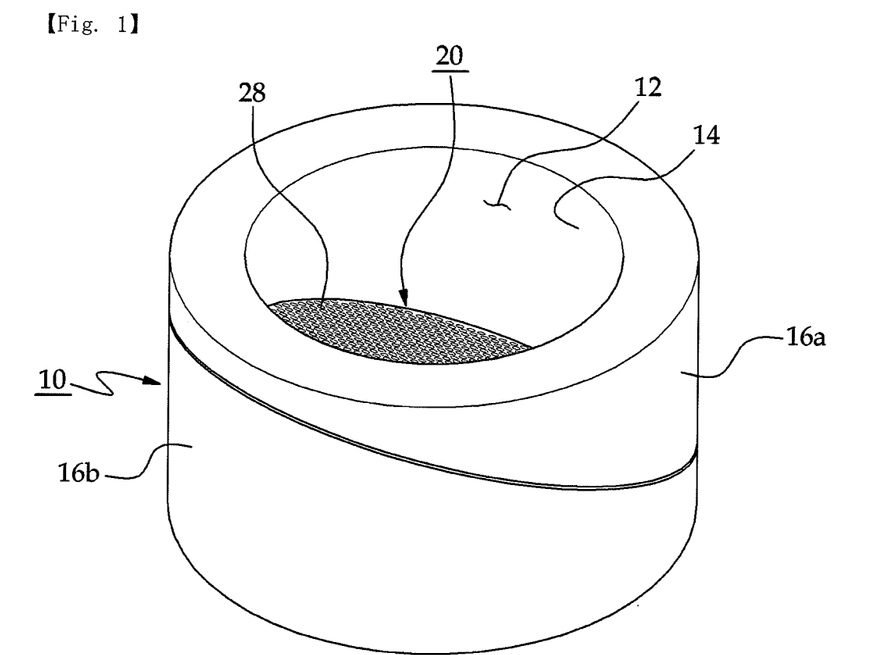
FIG. 1 is a perspective view showing the configuration of a cell collecting device according to one embodiment of the present invention.
Figure 2:
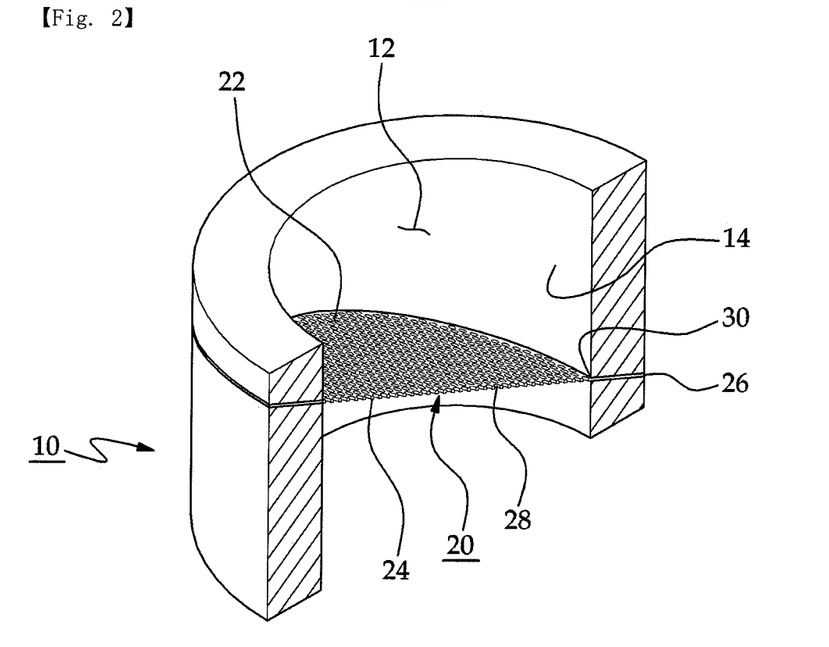
FIG. 2 is a partially cutaway perspective view of the cell collecting device shown in FIG. 1.
Figure 3:
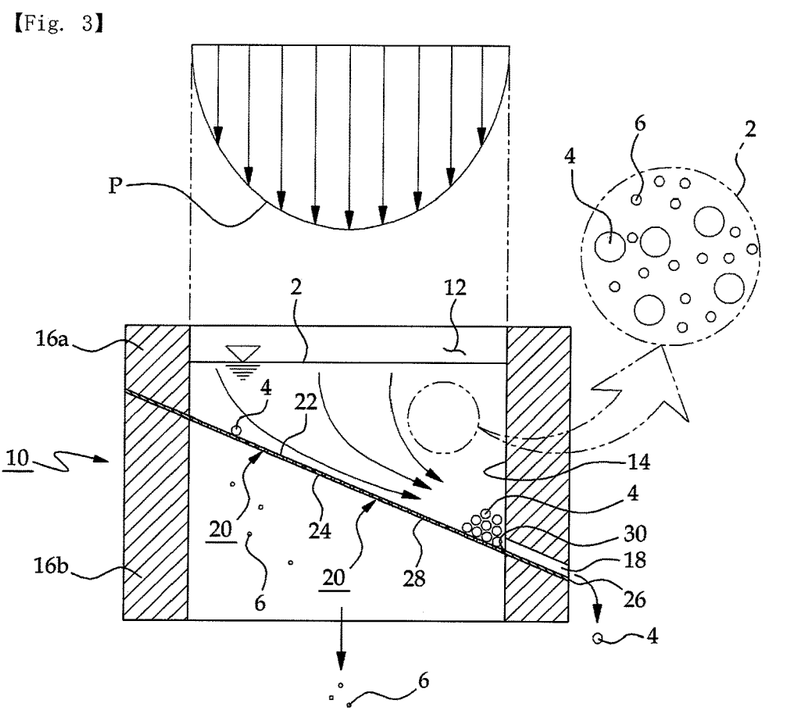
FIG. 3 is a section view of the cell collecting device shown in FIG. 1.

Referring first to FIGS. 1 through 3, a cell collecting device according to the present invention is configured to filter target cells 4 from non-target cells 6 contained in a fluid sample 2, thereby collecting the target cells 4. The fluid sample 2 includes physiological fluid such as saliva, sweat or urine of a human or an animal, blood and serum. In addition, the fluid containing target cells 4 such as cells or tissues of a human, an animal or a plant and the fluid containing viruses or bacteria may be selected as the fluid sample 2. If the blood is selected as the fluid sample 2, the cells of different sizes contained in the blood may become the target cells 4. Examples of the cells contained in the blood include red blood cells, white blood cells and cancer cells. In the embodiments of the present invention, the cancer cells may be selected as the target cells 4. The red blood cells and the white blood cells may be selected as the non-target cells 6.

The present cell collecting device includes a conduit 10 through which the fluid sample 2 can flow. The conduit 10 includes a tubular wall 14 defining a passage 12 through which a large amount of fluid sample 2 containing target cells 4 can flow smoothly. The passage 12 can be formed to have many different cross-sectional shapes such as a circular cross-sectional shape and a rectangular cross-sectional shape. The conduit 10 is divided into an upper conduit part 16a and a lower conduit part 16b. The upper conduit part 16a and the lower conduit part 16b are combined together by bonding, press-fit or thread coupling so as to define the passage 12.

The present cell collecting device further includes a screen filter 20 installed in the passage 12 of the conduit 10. The screen filter 20 includes a front surface 22, a rear surface 24, a peripheral edge 26 and a plurality of filtering holes 28 formed so as to filter the target cells 4. The filtering holes 28 are formed to have a dimension smaller than the diameter of the target cells 4. The screen filter 20 is preferably made of metal, e.g., stainless steel, nickel, aluminum or copper. The filtering holes 28 having a micrometer size can be formed by etching or electroforming through the use of a MEMS (Micro-Electro-Mechanical System) technology. The screen filter 20 is rigid enough not to be deformed by the pressure of the fluid sample 2 flowing through the passage 12.

The peripheral edge 26 of the screen filter 20 is interposed between the lower end of the upper conduit part 16a and the upper end of the lower conduit part 16b. The front surface 22 meets with the tubular wall 14. The screen filter 20 is shaped to guide the target cells 4 toward a boundary region 30 where the tubular wall 14 adjoins the front surface 22. While the peripheral edge 26 of the screen filter 20 is interposed between the upper conduit part 16a and the lower conduit part 16b in the present embodiment, the screen filter 20 may be arranged in the passage 12 such that the peripheral edge 26 thereof makes contact with the tubular wall 14.

The screen filter 20 is obliquely installed in the passage 12 along the flow direction of the fluid sample 2 so as to gather the target cells 4 in the boundary region 30 where the downstream end of the screen filter 20 meets with the tubular wall 14. In other words, the target cells 4 are gathered in the boundary region 30 existing between the downstream end portion of the screen filter 20 and the tubular wall 14. In the present embodiment, the slope of the screen filter 20 is set to ensure that the target cells 4 can flow down toward the boundary region 30 along the front surface 22 of the screen filter 20.

As shown in FIG. 3, the conduit 10 has an outlet 18 formed near the boundary region 30 and kept in communication with the boundary region 30. The target cells 4 gathered in the boundary region 30 can be collected by discharging the target cells 4 out of the conduit 10 through the outlet 18. The outlet 18 may be opened and closed by a well-known valve.

In the present cell collecting device configured as above, the fluid sample 2 is supplied to the upstream end of the conduit 10 by a fluid sample supply means (not shown). Examples of the fluid sample supply means include a syringe, a blood collection tube, a bag, a pack or other containers capable of storing a specified amount of fluid sample and supplying the fluid sample to the upstream end of the conduit 10. The fluid sample supply means may be formed of a syringe pump or a plunger pump.

If the fluid sample 2 is supplied to the upstream end of the conduit 10 as shown in FIG. 3, the target cells 4 contained in the fluid sample 2 flowing along the passage 12 cannot pass through the filtering holes 28 but obliquely move down along the front surface 22 toward the downstream end portion of the screen filter 20. Thus, the target cells 4 are gathered in the boundary region 30 where the downstream end of the front surface 22 meets with the tubular wall 14.

The flow velocity profile P of the fluid sample 2 shows such a pattern that the flow velocity becomes highest in the central region of the passage 12 and grows lower toward the tubular wall 14 due to the pile friction loss. The pressure is high and the flow velocity is low at the upstream end of the front surface 22 and the downstream end of the rear surface 24 adjacent to the tubular wall 14.

The target cells 4 filtered by the filtering holes 28 in the central region of the screen filter 20 where the flow velocity is highest rapidly flow down toward the downstream end of the screen filter 20 along the front surface 22. The non-target cells 6, e.g., red blood cells, rapidly pass through the filtering holes 28 in the central region of the screen filter 20. Accordingly, it is possible to prevent the filtering holes 28 from being clogged by the target cells 4 and the non-target cells 6. This makes it possible to maintain smooth flow of the fluid sample 2, thereby efficiently filtering the target cells 4 from the fluid sample 2.

The screen filter 20 of the present cell collecting device is formed into a linear shape as shown in FIG. 1. Alternatively, the screen filter 20 may be formed into a curvilinear shape with an apex point existing at the center, a monotonously increasing curvilinear shape or a monotonously decreasing curvilinear shape. In case of the screen filter having a curvilinear shape with an apex point existing at the center, the slope of the tangential line becomes gentlest in the central region of the screen filter and grows gradually larger toward the peripheral edge of the screen filter. For that reason, even if the flow velocity of the fluid sample 2 is not high in the central region of the passage 12, it is possible to efficiently gather the target cells 4 in a region near the tubular wall 14.

The target cells 4 gathered in the boundary region 30 can be collected by discharging the target cells 4 out of the conduit 10 through the outlet 18. In this collecting process, the target cells 4 discharged out of the conduit 10 may be received in a test tube or a culture dish.

Figure 4:
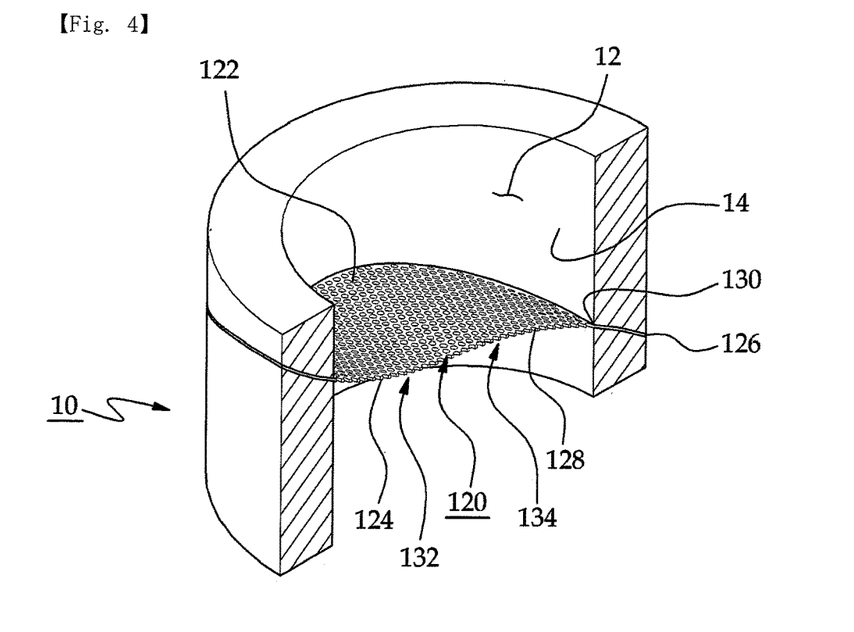
FIG. 4 is a partially cutaway perspective view showing one modified example of a screen filter employed in the present cell collecting device.
Figure 5:
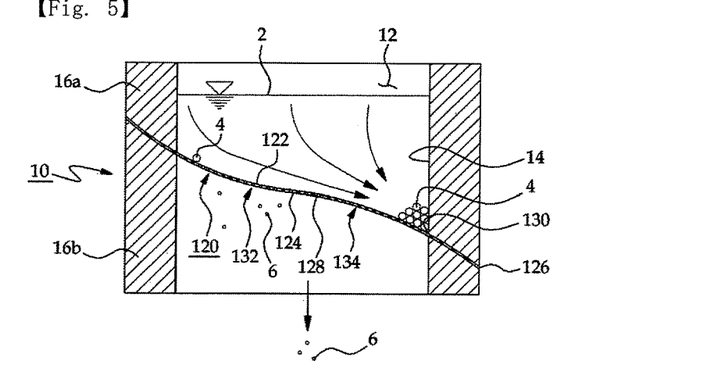
FIG. 5 is a section view of the screen filter shown in FIG. 4.

FIGS. 4 and 5 show one modified example of the screen filter employed in the present cell collecting device. Referring to FIGS. 4 and 5, the screen filter 120 according to one modified example includes a front surface 122, a rear surface 124, a peripheral edge 126 and a plurality of filtering holes 128 formed so as to filter the target cells 4. The screen filter 120 is obliquely installed in the passage 12 along the flow direction of the fluid sample 2 so as to gather the target cells 4 in a boundary region 130 where the downstream end of the screen filter 120 meets with the tubular wall 14.

The screen filter 120 is formed into a double-curve shape to have a concave portion 132 positioned more upward than the center of the screen filter 120 and a convex portion 134 positioned more downward than the center of the screen filter 120. The concave portion 132 and the convex portion 134 are connected to each other in a smooth wave form. In the concave portion 132, the non-target cells 6 can smoothly pass through the filtering holes 28. The target cells 4 are rapidly moved toward the boundary region 30 across the convex portion 134 and are gathered in the boundary region 30. It is therefore possible to separate the target cells 4 from the non-target cells 6 and to gather the target cells 4 in a region near the tubular wall 14.

In the screen filter 120 of a double-curve shape including the concave portion 132 and the convex portion 134, the slope of the tangential line is changed depending on the curvature of the screen filter 120. The slope of the tangential line affects the efficiency of guiding the target cells 4 toward the tubular wall 14. The collection efficiency of the target cells 4 can be increased by appropriately changing the curvature of the screen filter 120 depending on the flow velocity profile of the fluid sample 2.

Figure 6:
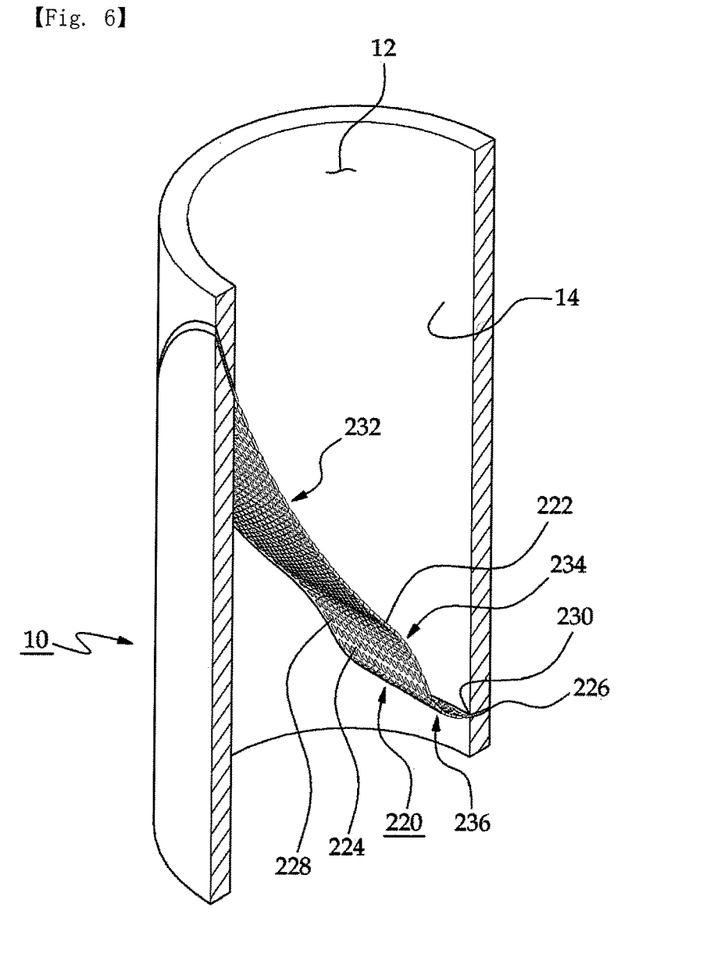
FIG. 6 is a partially cutaway perspective view showing another modified example of a screen filter employed in the present cell collecting device.
Figure 7:
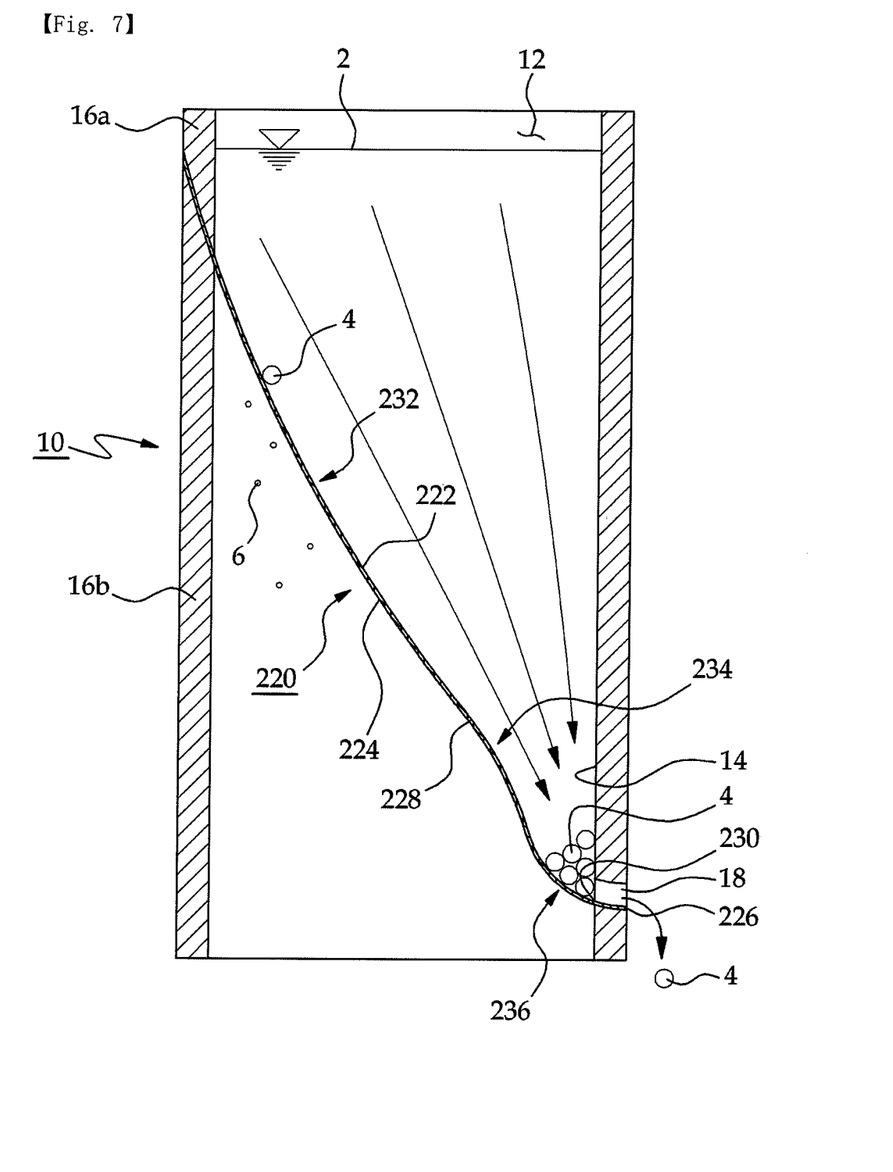
FIG. 7 is a section view of the screen filter shown in FIG. 6.

FIGS. 6 and 7 show another modified example of the screen filter employed in the present cell collecting device. Referring to FIGS. 6 and 7, the screen filter 220 according to another modified example includes a front surface 222, a rear surface 224, a peripheral edge 226 and a plurality of filtering holes 228 formed so as to filter the target cells 4. The screen filter 220 is obliquely installed in the passage 12 along the flow direction of the fluid sample 2 so as to gather the target cells 4 in a boundary region 230 where the downstream end of the screen filter 220 meets with the tubular wall 14.

The screen filter 220 includes a concave portion 232 gently curved from the upstream end toward the downstream end and a convex portion 234 extending further downward from the concave portion 232. The screen filter 220 further includes a concave trap 236 formed at the most downstream end of the screen filter 220 so as to accommodate the target cells 4. The trap 236 is formed into a pocket shape so as to gather the target cells 4 in between the tubular wall 14 and the trap 236. The concave portion 232 and the convex portion 234 serve to guide the target cells 4 toward the trap 236. The target cells 4 move downward along the front surface 222 and come into the trap 236. Accordingly, it is possible to separate the target cells 4 from the non-target cells 6 and to efficiently gather the target cells 4 in the trap 236. The target cells 4 gathered in the trap 236 can be discharged out of the conduit 10 through the outlet 18.

Figure 8:
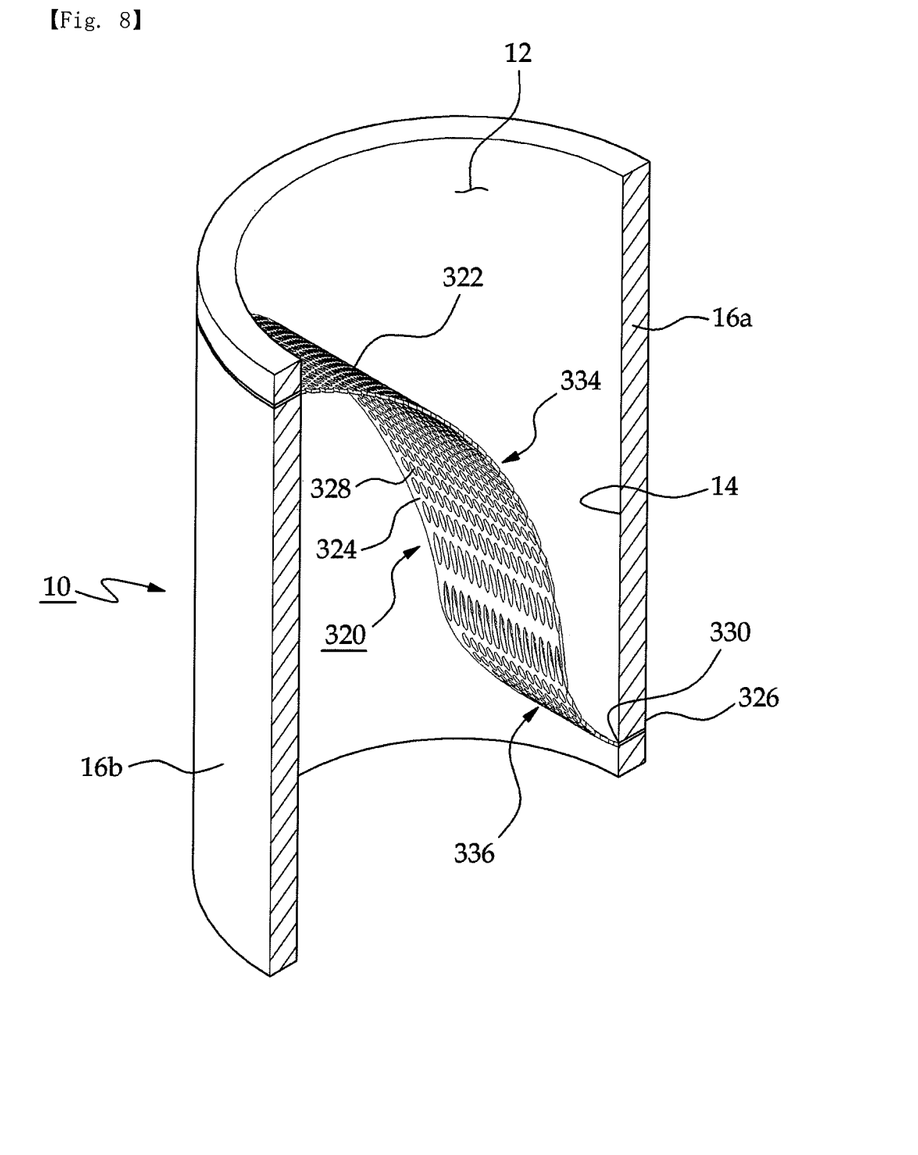
FIG. 8 is a partially cutaway perspective view showing a further modified example of a screen filter employed in the present cell collecting device.
Figure 9:
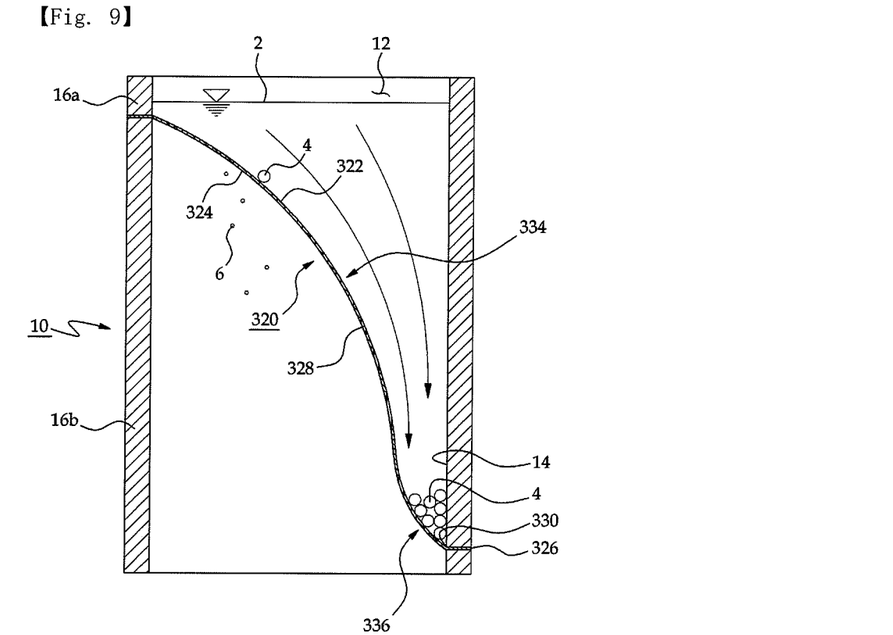
FIG. 9 is a section view of the screen filter shown in FIG. 8.

FIGS. 8 and 9 show a further modified example of the screen filter employed in the present cell collecting device. Referring to FIGS. 8 and 9, the screen filter 320 according to a further modified example includes a front surface 322, a rear surface 324, a peripheral edge 326 and a plurality of filtering holes 328 formed so as to filter the target cells 4.

The screen filter 320 is obliquely installed in the passage 12 along the flow direction of the fluid sample 2 such that the target cells 4 moving down along the front surface 322 are gathered in a trap 336. The screen filter 320 includes a convex portion 334 formed between the trap 336 and the upstream end of the screen filter 320 so as to bulge obliquely upward. The convex portion 334 serves to guide the target cells 4 toward the trap 336. It is therefore possible to separate the target cells 4 from the non-target cells 6 and to gather the target cells 4 in the trap 336.

Figure 10:
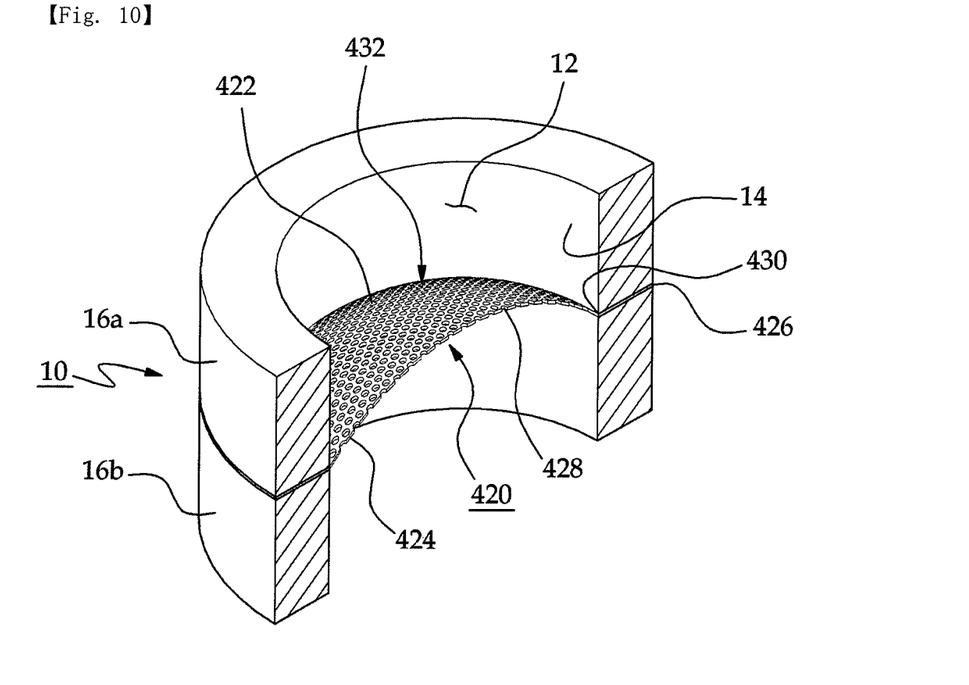
FIG. 10 is a partially cutaway perspective view showing a still further modified example of a screen filter employed in the present cell collecting device.
Figure 11:
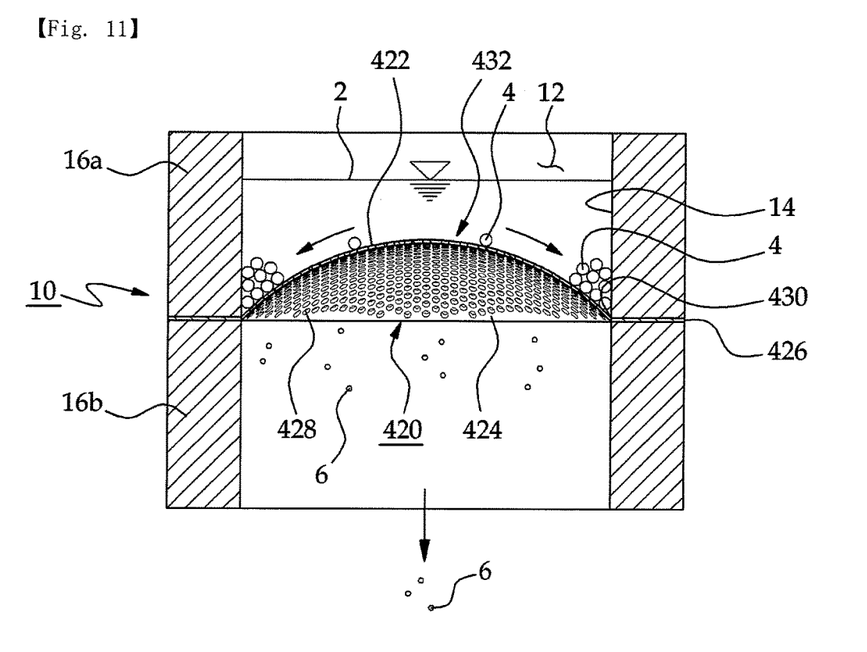
FIG. 11 is a section view of the screen filter shown in FIG. 10.

FIGS. 10 and 11 show a still further modified example of the screen filter employed in the present cell collecting device. Referring to FIGS. 10 and 11, the screen filter 420 according to a still further modified example includes a front surface 422, a rear surface 424, a peripheral edge 426 and a plurality of filtering holes 428 formed so as to filter the target cells 4. The peripheral edge 426 is interposed between the upper conduit part 16a and the lower conduit part 16b and is arranged on a plane orthogonal to the tubular wall 14.

The screen filter 420 includes a convex portion 438 formed so as to guide the target cells 4 toward a boundary region 430 where the downstream end of the screen filter 420 meets with the tubular wall 14. The convex portion 438 is formed into a substantially dome-like shape such that the target cells 4 are guided from the central peak of the convex portion 438 toward the boundary region 430. The target cells 4 that cannot pass through the filtering holes 428 are moved down along the convex portion 438 toward the boundary region 430. The target cells 4 are gathered in the boundary region 430, i.e., at the edge of the convex portion 438. This prevents the filtering holes 428 from being clogged by the target cells 4. While the convex portion 438 is formed into a substantially dome-like shape in the present modified example, the present invention is not limited thereto. Alternatively, the convex portion 438 may be formed into a conical shape, a triangular pyramidal shape, a rectangular pyramidal shape or other shapes suitable for guiding the target cells 4 from the center of the passage 12 toward the tubular wall 14.

Figure 12:
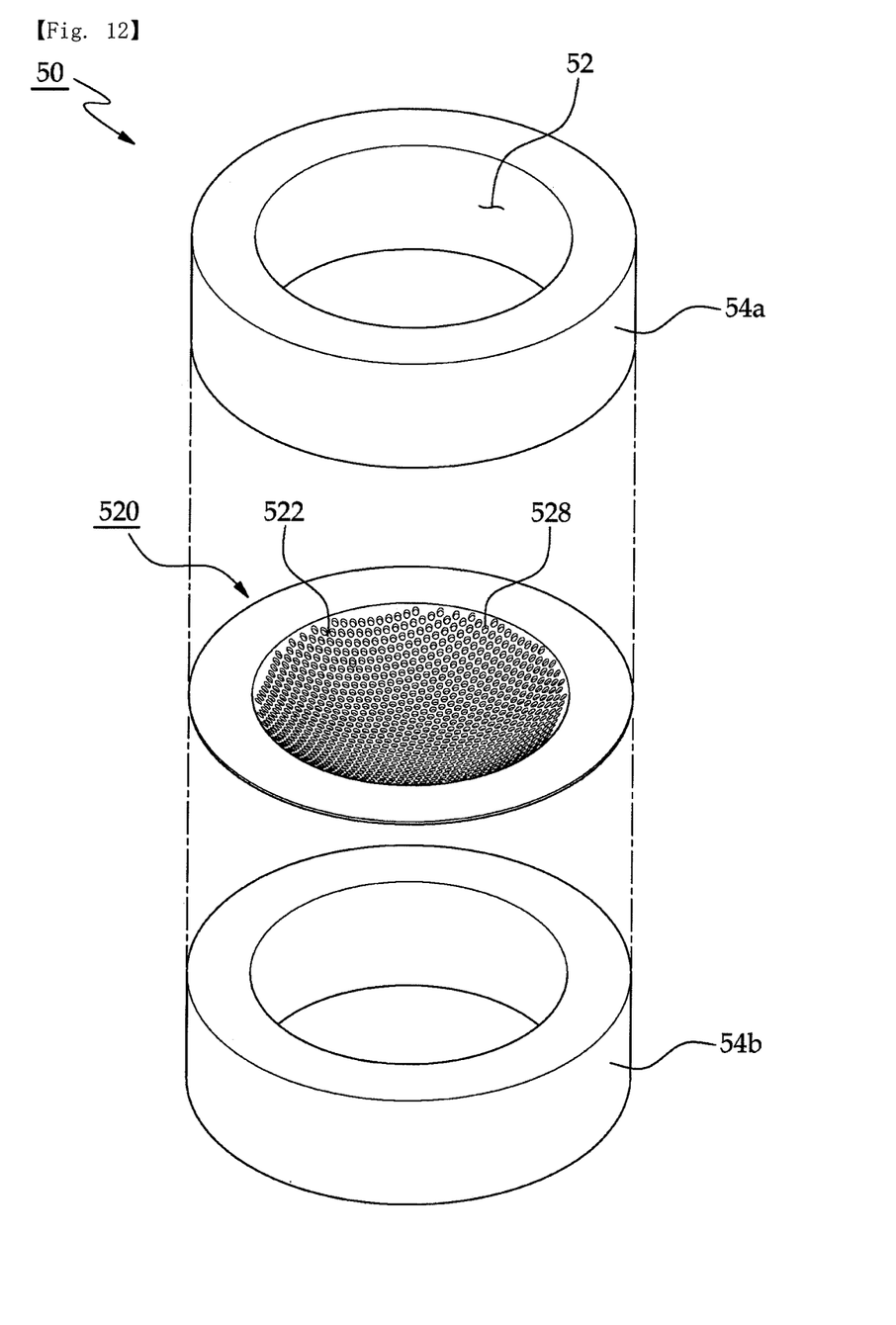
FIG. 12 is an exploded perspective view showing a cell collecting device according to another embodiment of the present invention.
Figure 13:
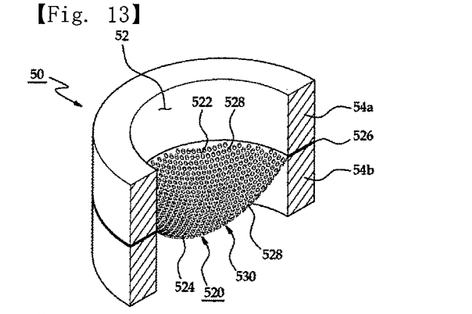
FIG. 13 is a partially cutaway perspective view of the cell collecting device shown in FIG. 12.
Figure 14:
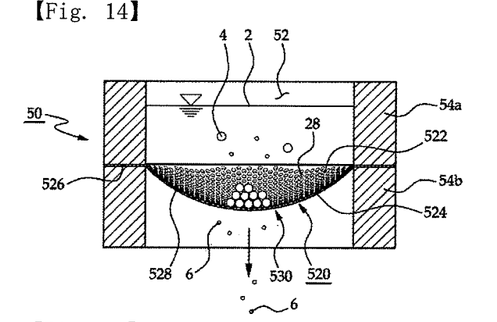
FIG. 14 is a section view of the cell collecting device shown in FIG. 12.

FIGS. 12 through 14 show a cell collecting device according to another embodiment of the present invention. Referring to FIGS. 12 through 14, the cell collecting device according to another embodiment includes a conduit 50 through which a fluid sample 2 can flow. The conduit 50 has a passage 52 through which the fluid sample 2 can pass. The conduit 50 is divided into an upper conduit part 54a and a lower conduit part 54b. The upper conduit part 54a and the lower conduit part 54b are combined together by bonding, press-fit or thread coupling so as to define the passage 52. The passage 52 can be formed into many different cross-sectional shapes such as a circular cross-sectional shape and a rectangular cross-sectional shape so as to smoothly pass the fluid sample 2 therethrough.

The present cell collecting device further includes a screen filter 520 installed in the passage 52 of the conduit 50 so as to filter the target cells 4. The screen filter 520 includes a front surface 522, a rear surface 524, a peripheral edge 526 and a plurality of filtering holes 528 formed so as to filter the target cells 4. The peripheral edge 526 of the screen filter 520 is interposed between the lower end of the upper conduit part 54a and the upper end of the lower conduit part 54b. Alternatively, the screen filter 520 may be press-fitted to the passage 52 so that the peripheral edge 526 can make contact with the inner circumferential surface of the conduit 50. While the screen filter 520 shown in FIG. 12 has a circular shape, the present invention is not limited thereto. The shape of the screen filter 520 may be appropriately changed to, e.g., a rectangular shape or an elliptical shape, depending on the shape of the passage 52.

The filtering holes 528 are formed to have a dimension smaller than the diameter of the target cells 4. The screen filter 520 is preferably made of metal, e.g., stainless steel, nickel, aluminum or copper. The filtering holes 528 having a micrometer size can be formed by etching or electroforming through the use of a MEMS (Micro-Electro-Mechanical System) technology. The screen filter 520 is rigid enough not to be deformed by the pressure of the fluid sample 2 flowing through the passage 52.

The screen filter 520 is shaped to guide the target cells 4 toward a specified region along the front surface 522. The screen filter 520 includes a concave portion 530 formed to gather the target cells 4 in the central region thereof. The concave portion 530 is formed into a substantially hemispherical shape. Alternatively, the concave portion 530 may be formed into a conical tube shape, a triangular pyramidal tube shape, a rectangular pyramidal tube shape or other shapes having a cross section gradually decreasing toward the downstream end of the conduit 50. Moreover, the concave portion 530 may be formed into many other shapes so that the target cells 4 can be gathered in the central region of the screen filter 520.

In the present cell collecting device configured as above, the fluid sample 2 is supplied to the upstream end of the conduit 50 by a fluid sample supply means (not shown). Examples of the fluid sample supply means include a syringe, a blood collection tube, a bag, a pack or other containers capable of storing a specified amount of fluid sample and supplying the fluid sample to the upstream end of the conduit 50. The fluid sample supply means may be formed of a syringe pump or a plunger pump.

If the fluid sample 2 is supplied to the upstream end of the conduit 50 as shown in FIG. 14, the target cells 4 contained in the fluid sample 2 flowing along the passage 52 cannot pass through the filtering holes 528 but obliquely move down along the front surface 522 toward the central region of the concave portion 530. Thus, the target cells 4 are gathered in the central region of the concave portion 530. Non-target cells 6, e.g., red blood cells, can rapidly pass through the filtering holes 528. Since the target cells 4 are gathered in the central region of the concave portion 530, it is possible to collect the target cells 4 with ease. In particular, cancer cells contained in the blood can be gathered in a specified place and collected in an efficient manner.

Figure 15:
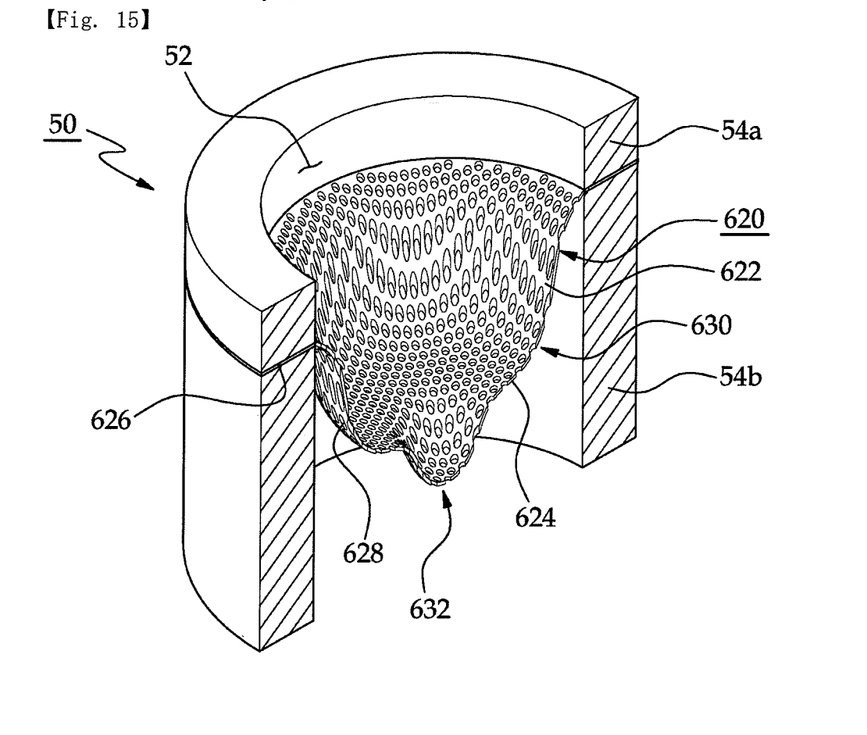
FIG. 15 is a partially cutaway perspective view showing a cell collecting device according to a further embodiment of the present invention.
Figure 16:
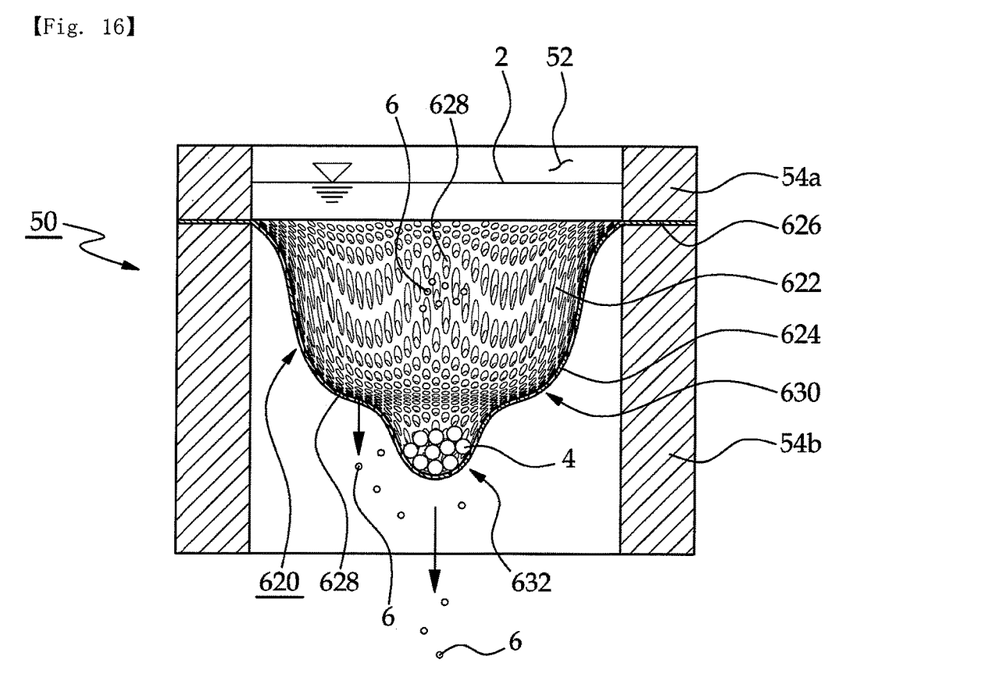
FIG. 16 is a section view of the cell collecting device shown in FIG. 15.

FIGS. 15 and 16 show a cell collecting device according to a further embodiment of the present invention. Referring to FIGS. 15 and 16, the cell collecting device according to a further embodiment includes a conduit 50 having a passage 52 defined therein and a screen filter 620 installed in the passage 52 of the conduit 10. The screen filter 620 includes a front surface 622, a rear surface 624, a peripheral edge 626 and a plurality of filtering holes 628 formed so as to filter the target cells 4.

The screen filter 620 includes a concave portion 630 formed to guide the target cells 4 downward along the front surface 622 and a trap 632 formed at the center of the concave portion 630 so as to gather the target cells 4. The trap 632 is formed into a pocket shape so as to hold the target cells 4 therein. The target cells 4 contained in the fluid sample 2 are moved downward along the concave portion 630 and are gathered in the trap 632. It is therefore possible to separate the target cells 4 from the non-target cells 6 and to gather the target cells 4 in the trap 632.

The target cells 4 filtered and gathered in the trap 632 can be discharged out of the trap 632 through the passage 52 by supplying a solution, e.g., water, into the passage 52 in a backward or forward direction. The target cells 4 discharged through the passage 52 may be received in a container such as a test tube or a culture dish. Since the target cells 4 are filtered from the fluid sample 2 by the screen filter 620 and then detached from the screen filter 620 by supplying the solution, it is possible to efficiently collect live cancer cells from the human blood.

While certain preferred embodiments of the invention have been described above, the scope of the present invention is not limited to these embodiments. It will be apparent to those skilled in the art that various changes, modifications and substitutions may be made without departing from the scope of the invention defined in the claims. Such changes, modifications and substitutions shall be construed to fall within the scope of the present invention.

What is claimed is:

1. A method of collecting cells from a fluid sample, the method comprising:
    providing a cell collection device comprising a first body, a second body and a screen device, the first body comprising a first sidewall defining a first conduit, the first sidewall having a first bottom surface, the second body comprising a second sidewall defining a second conduit, the second sidewall having a second top surface and a second bottom surface, the screen device comprising a screen portion with a plurality of pores, wherein the first body is placed over the second body such that the first bottom surface of the first sidewall faces the second top surface of the second sidewall and further such that the first and second conduits are aligned to provide a unitary conduit, wherein the screen device is engaged with at least one of the first and second body such that at least part of the screen portion is placed inside the unitary conduit;
    providing a fluid composition comprising target cells that are large enough to not pass through the plurality of pores;
    pouring the fluid composition from over the cell collection device into the unitary conduit such that the fluid composition flows downward, wherein at least part of the target cells do not pass through the plurality of pores and stays over the screen portion while at least part of the rest of the fluid composition passes downward through the plurality of pores of the screen portion; and
    subsequently, collecting at least part of the target cells that has not passed through the plurality of pores,
    wherein the second bottom surface is generally perpendicular to a downward flow direction defined by the unitary conduit, wherein the screen portion is slanted relative to the second bottom surface, wherein the slanted screen portion provides the lowest region on the screen portion, wherein at least part of the target cells slide over the screen portion toward the lowest region, wherein the lowest region on the screen portion in adjacent to an inner surface of the first sidewall, wherein the cell collection device comprises a through-hole next to the lowest region on the screen portion for discharging at least part of the target cells from unitary conduit therethrough, wherein at least part of the target cells are collected from outside the through-hole.

2. The method of claim 1, wherein the screen device further comprises a perimeter portion surrounding the screen portion, wherein at least part of the perimeter portion is interposed between the first bottom surface and the second top surface.

3. The method of claim 1, wherein the second bottom surface is generally perpendicular to a downward flow direction defined by the unitary conduit, wherein the screen portion comprises a slanted portion slanted relative to the second bottom surface, wherein subsequent to pouring, at least part of the target cells slides over the slanted portion toward a lower region from a higher region thereon.

4. The method of claim 1, wherein the slanted screen portion comprises an inflection point in a cross-section taken by a plane generally parallel to the downward flow direction.

5. The method of claim 1, wherein the lowest region on the screen portion is adjacent to an inner surface of the first sidewall, wherein at least part of the target cells are collected from the lowest region.

6. The method of claim 1, wherein the screen device further comprises a perimeter portion extending into the through-hole from the lowest region.

7. The method of claim 1, wherein the through-hole is defined with a portion of the second top surface and a cutout portion of the first sidewall.

8. The method of claim 1, wherein the second bottom surface is generally perpendicular to a downward flow direction defined by the unitary conduit, wherein the screen portion comprises one or more of a upwardly convexed portion and a downwardly concaved portion.

9. The method of claim 1, wherein the screen device further comprises a perimeter portion extending into the through-hole from the lowest region, wherein the through-hole is defined with a portion of the second top surface and a cutout portion of the first sidewall.

10. The method of claim 9, wherein the portion of the second top surface is slanted relative to the second bottom surface to facilitate discharging of at least part of the target cells via the through-hole.

\* \* \* \* \*